United States Patent
Rhodes et al.

(10) Patent No.: US 6,238,689 B1
(45) Date of Patent: May 29, 2001

(54) INTESTINAL ABSORPTION OF NICOTINE TO TREAT NICOTINE RESPONSIVE CONDITIONS

(75) Inventors: John Rhodes, Cardiff; Brian K. Evans, Dinas Powis; Peter Rhodes, Nomansland, all of (GB); William J. Sandborn, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/147,516

(22) PCT Filed: Jul. 16, 1997

(86) PCT No.: PCT/GB97/01938

§ 371 Date: Apr. 30, 1999

§ 102(e) Date: Apr. 30, 1999

(87) PCT Pub. No.: WO98/02188

PCT Pub. Date: Jan. 22, 1998

(30) Foreign Application Priority Data

Jul. 16, 1998 (GB) .................................................. 9614902

(51) Int. Cl.[7] .............................. A61K 9/22; A61K 9/32; A61K 9/10

(52) U.S. Cl. .................... 424/436; 514/813; 514/879; 424/468; 424/482

(58) Field of Search .............................. 424/484; 514/813

(56) References Cited

U.S. PATENT DOCUMENTS 5,889,028 * 3/1999 Sandborn et al. .................... 514/343

FOREIGN PATENT DOCUMENTS

| B81712/87 | 6/1988 | (AU) . |
| 3645036 | 1/1989 | (DE) . |
| 377520 | 7/1990 | (EP) . |
| 904874 | 9/1962 | (GB) . |
| WO97/28801 | 8/1997 | (WO) . |

OTHER PUBLICATIONS

Gong, et al., Pharmaceutical Research, vol. 13, No. 9, p. S222, Abstract PT6263 (1996).

Green, et al., Clinical Pharmacology and Therapeutics, vol. 61, No. 3, pp 340–348 (Mar. 1997).

* cited by examiner

Primary Examiner—Peter F. Kulkosky

(57) ABSTRACT

A delayed and sustained release composition of an additive and/or toxic agent such as nicotine is delivered systemically in therapeutic amounts while avoiding the peak plasma levels which gives rise to addiction and/or toxic side effects. The composition is delivered for absorption predominantly from the colon.

12 Claims, 3 Drawing Sheets

INTESTINAL ABSORPTION OF NICOTINE TO TREAT NICOTINE RESPONSIVE CONDITIONS

The present invention relates to the use of nicotine composition delivered for absorption from the intestine, particularly the ileum and colon, for the treatment of nicotine responsive conditions particularly schizophrenia, Alzheimer's disease, Tourette's syndrome, Parkinson's disease, depression (particularly associated with cessation of smoking), inflammatory skin conditions, and as an aid to cease smoking.

Cigarette smoking has been reported as altering the inflammatory response in the skin following application of irritants and rubefacients (Mills et al, BMJ 1993;307:911). In a follow up study, Mills administered nicotine via a transdermal delivery system and was found to suppress the cutaneous inflammatory response to sodium lauryl sulphate (irritant) and UVB radiation, as well as reactive hyperaemia following arterial occlusion (Workshop on Nicotine as a Therapeutic Agent—May 15, 1996, Frankfurt, Germany). In the same workshop, Sandberg et al reported that administration of nicotine (either 2 mg nicotine gum or 7 mg transdermal nicotine patch) along with neuropleptics produce a decrease in tic symptoms in patients suffering from Tourette's syndrome. A beneficial response of Alzheimer's and Parkinson's disease patients to nicotine was also reported at the workshop.

However, nicotine has a substantial effect on the cardiovascular system including increased heart rate and blood pressure resulting in greater myocardial work and oxygen requirement and coronary vasocontriction. Nicotine has also be purported to activate platelets and to adversely affect blood lipids, thereby promoting atherosclerosis and increasing the risk of acute coronary events. Furthermore nicotine from tobacco products has also been associated with an increased risk of cancer and cerebral haematoma.

Known delivery routes for nicotine are via cigarette smoking, inhalers, nasal spray, polyacrylic gum and transdermal patch. Inhalers and nasal sprays deliver nicotine rapidly to the blood plasma in high peak concentrations and can therefore give rise to addictive cravings similar to cigarette smoking. The use of nicotine gum and transdermal patches are reported at the aforementioned Nicotine Workshop, and are used extensively to aid in the cessation of smoking. However long term administration of a nicotine patch is limited by a relatively high rate of dermatological side effects, especially in the elderly. Patients have also reported side effects such as nausea, headaches, tremor and vomiting, thereby again limiting patient compliance. Polyacrylic gum again relies heavily on good patient compliance. The amount of nicotine delivered depends on the rate and length of chewing and therefore it is difficult to achiever a controlled uniform plasma concentration of nicotine.

It is an object of the present invention to obviate or mitigate the aforesaid disadvantages.

It is a further object to provide for delivery of nicotine which is convenient and where side effects of nicotine is limited, while still providing a beneficial effect on conditions susceptible to treatment with nicotine.

The inventors have now found that the blood plasma concentration of nicotine can be controlled to therapeutic levels while limited the adverse side-effects if nicotine is absorbed from the small or large intestine. For example nicotine can be delivered rectally, such as by an enema, to the large intestine or as a post-gastric delayed release oral (DRO) composition to the small and/or large intestine. In this way the nicotine is absorbed more slowly into the blood plasma over a sustained time period thereby decreasing the peak plasma concentrations which typically induces nicotine dependency. It also avoids the dermatological side-effects of a transdermal patch, and the uncertain effectiveness of nicotine chewing gum. Thus therapeutic levels of nicotine can be delivered to treat the aforementioned conditions while reducing the adverse side-effects normally associated with nicotine.

Accordingly in a first aspect of the invention there is provided the use of nicotine or a pharmacologically acceptable derivative or metabolite thereof in the preparation of a medicament which is adapted for absorption from the small and/or large intestine for the treatment or prophylaxis of inflammatory skin conditions, schizophrenia, Alzheimer's disease, Parkinson's disease, Tourette's syndrome, depression, or to assist in the cessation of smoking. In fact, nicotine could be used therapeutically in any disease state in which an association with non-smoking or smoking status would suggest a therapeutic role for nicotine. For the avoidance of doubt, absorption from the small and/or large intestine includes from the pylorus to the anus.

Examples of inflammatory skin conditions susceptible to the invention are acne, reigacne vulgaris and rosacea. With Alzheimer's patients, the invention will typically improve their attentional function. Depression, particularly associated with the cessation of smoking, is susceptible to treatment with the invention.

A further aspect of the invention comprises a method for the treatment of nicotine responsive condition, disclosed herein, comprising administering to the patient an effective amount of a rectally administrable or delayed release oral (DRO) DRO composition as defined in the first aspect of the invention.

Co-pending International No. PCT/GB97/00369 and U.S. application Ser. Nos. 08/605,319 and 08/794,668 relate to the use of nicotine delivered for sustained release from the colon for the treatment of inflammatory bowel disease, and therefore this nicotine responsive condition is not within the scope of the present condition.

Although there is some benefit in having absorption of nicotine from anywhere in the small or large intestine, it is most preferred that absorption occurs predominantly in the colon. This in the case of a post-gastric delayed release oral (DRO) composition, the composition will pass through the small intestine in about 4 to 8 hours and will then reside in the colon for about 48 hours. Furthermore nicotine is absorbed more slowly in the colon than in the small intestine. Therefore nicotine delivered for absorption predominantly in the colon will be absorbed more slowly over a sustained period and will give rise to a more uniform blood plasma concentration, and will reduce the peak concentration of nicotine which otherwise cause dependence and adverse side-effects.

By predominant absorption from the colon, we mean to include at least 70%, more preferably at least 80%, such as at least 85% or at least 90% of the total dose of nicotine.

In a preferred embodiment, a DRO composition is delivered for dissolution in the ileum, more particularly the terminal ileum so that most of the nicotine would be released and absorbed in the colon.

The most preferred form of the invention is a sustained and post-gastric delayed released composition. In this form, the effect of the nicotine being absorbed more slowly and at more uniform concentration levels into the bloodstream from the small and/or large intestine, is enhanced because the composition also controls the release of the nicotine over a sustained time interval. This form of the invention is of particular benefit, where most of the nicotine is released and absorbed in the colon i.e. the composition resides here for the longest time period. Thus in a preferred embodiment the invention relates to use of nicotine given orally as a sustained release DRO composition (advantageously having an enteric coating) for the treatment of nicotine responsive conditions.

Various sustained release compositions of nicotine are described later and include nicotine being present as a nicotine-polyacrylate complex, nicotine is an ampiphilic polyglycolized glyceride matrix, and using various enteric coated microgranules containing nicotine in an enteric coated capsule. A preferred form of saturated polyglycolized glyceride is Gelucire™, particular Gelucire 44/14 and 53/10.

By pharmacologically acceptable derivatives and metabolites of nicotine we mean derivatives which exhibit pharmacotherapeutic properties similar to said active agent. This includes pharmacologically acceptable salts, esters and salts of such esters.

Any pharmacologically acceptable derivative or metabolite of nicotine which exhibits pharmacotherapeutic properties similar to nicotine may be used in practising the invention. Such derivatives and metabolites are known in the art (Glenn et al J. Org. Chem., 43:2860–2870 (1978); Dominiak et al., Klin Wochenschr, 63:90–92 (1985)) and include nicotine oxide and cotinine.

A particular characteristic property of nicotine is its ability to form salts with almost any acid and double salts with many metals and acids. The acids that may be used to prepare the pharmaceutically acceptable acid salts of nicotine are those that form non-toxic acid salts, i.e., salts containing pharmacologically acceptable anions, such as hydrochloride, hydrobromide, hydroiodide, nitrate, sulphate or bisulphate, succinate, maleate, fumarate, bitartrate, gluconate, saccharate, benzoate, methanesulphonate, ethanesulphonate, benzenesulphonate, p-toluene sulphonate, camphorate and pamoate salts. Particularly preferred are the tartrate and bitartrate salts.

Preferably nicotine is present in a complex with a polyacrylic acid polymer to form a nicotine-polyacrylate complex, preferably a water-soluble complex.

Preferably, the polyacrylate is a carbomer, such as those described in the British Pharmacopoeia and defined in CAS 54182-57-9. Carbomers are synthetic high molecular weight polymers of acrylic acid cross-linked with allylsucrose, and contain 56 to 68% carboxylic acid groups. When used in accordance with an oral dosage form of the invention the carbomers hydrate and swell to form a gel, which retards the nicotine release and absorption.

A complex of bismuth and carbomer is disclosed in EP-A-0540613.

Convenient modes of administration to deliver the sustained release composition for absorption from the colon are rectal compositions such as enemas and suppositories, and DRO compositions such as enteric coated tablets, capsules, powder or granules.

Typical enema formulations comprise an effective amount of nicotine dissolved or dispersed in a suitable aqueous flowable carrier vehicle. The carrier vehicle is preferably thickened with natural or synthetic thickeners such as gums, acrylates or modified celluloses. The formulation can also comprise an effective amount of a lubricant such as a natural or synthetic fat or oil, e.g. a tris-fatty acid glycerate or lecithin. Nontoxic nonionic surfactants can also be included as wetting agents and dispersants. Unit dosages of enema formulations can be administered from prefilled bags or syringes. The carrier vehicle may also comprise an effective amount of a foaming agent such as n-butane, propane or i-butane. Such formulations can be delivered from a preloaded syringe pressurised container, so that the vehicle is delivered to the colon as a foam, which inhibits its escape from the target site.

A dosage form of nicotine adapted for either rectal or oral delivery may also be complexed with a suspending or thickening agent to prolong release of the dosage form of nicotine. Such agents include methacrylic acid polymer or acrylic acid polymers, preferably carbomers (carboxypolymethylene) which are synthetic high molecular weight acrylic acid polymers crosslinked with polyfunctional moieties such as polyallylsucrose. Generally, carbomers comprise 50 to 70% carboxylic acid groups.

In a preferred embodiment, an active agent/carbomer complex may be administered rectally as liquid enemas. Liquid enemas are prepared essentially as described above by forming an effective amount of a nicotine/carbomer complex in a suitable flowable liquid carrier. The carrier vehicle is preferably thickened with thickeners and can also comprise an effective amount of a lubricant. Unit dosages of enema formulations can be administered from prefilled bags or syringes.

The pH of the enema should be 3.0 to 3.5 before a buffering solution is added to raise the pH to between 4.5 to 5.5, ideally about pH 5.0 (at which patients feel comfortable).

In a carbomer formulation this can be achieved by adding quantities of a suitable amine protein acceptor to the preparation. At the same time such a preparation also neutralises some of the carbomer molecules thereby increasing the viscosity. Preferably trometamol is used as a buffering and thickening agent in an enema composition. On average each 100 ml of enema requires about 6 ml (viscosity 4.5 to 7.5 mNm) of a 1% solution of trometamol to give a final acceptable pH of about 5 and viscosity of 3 to 6.5 mNm, ideally 4.0 mNm.

In general where the nicotine is administered rectally, a suitable dose will be in the range of from 0.001 to 1.5 mg/Kg, preferably in the range of 0.01 to 0.20 mg/Kg, most preferably in the range of 0.04 to 0.10 mg/Kg, calculated as nicotine in the free base form. Preferably, nicotine is rectally administered once or twice daily.

When the active agent is administered orally via a tablet, capsule or granules, preferably the dosage form will have an enteric coating which dissolves in the ileum so that the active agent can predominantly be absorbed from the colon.

In general, where the nicotine is administered orally, a suitable dose will be in the range of from 0.001 to 1.5 mg per day preferably in the range of 0.01 to 20 mg per day most preferably in the range of 0.04 to 15 mg per day, calculated as nicotine in the free base form. Preferably, nicotine is orally administered 1 to 4 times daily, for example 3–4 times daily, although more frequent dosing is contemplated where hourly dosing is desired.

The compound is conveniently administered orally in unit dosage form; for example, containing 1 to 36 mg, conveniently 3 to 30 mg, such as 6 to 30 mg, and such as 15 to 30 mg of active ingredient per unit dosage form. In a preferred embodiment of the invention 3 mg to 6 mg was useful.

An effective amount of nicotine can be administered to the intestine, preferably the colon of the patient by oral ingestion of a unit dosage form such as a pill, tablet, powder or capsule, comprising an effective amount of nicotine which is enterically coated so as to be released from the unit dosage form in the lower intestinal tract, e.g., in the ileum and in the colon of the patient. Enteric coatings remain intact in the stomach, but will dissolve and release the contents of the dosage form once it reaches the region where the pH is optimal for dissolution of the coating used. The purpose of an enteric coating is to substantially delay the release of the nicotine until it reaches its target site of action in the ileum or colon.

Thus, a useful enteric coating is one that remains intact in the low pH environment of the stomach, but readily dissolved when the optimum dissolution pH of the particular coating is reached. This can vary between pH 3 to 7.5 depending upon the chemical composition of the enteric coating, but is preferably between about pH 6.8 and pH 7.2. The thickness of the coating will depend upon the solubility characteristics of the coating material and the site to be treated.

In general coating thicknesses of about 25 to 200 $\mu$m, and especially 75 to 150 $\mu$m, are preferred using about 3 to 25 mg, preferably 8 to 15 mg of acidic coating material per $cm^2$ of tablet or capsule surface. The precise coating thickness will however depend upon the solubility characteristics of the acidic material used and site to be treated.

When used in accordance with an oral dosage form of the invention the carbomers hydrate and swell to form a gel, which retards the nicotine release and absorption.

The most extensively used polymer for enteric coating is cellulose acetate phthalate (CAP). However, CAP has an optimum dissolution pH greater than 6, thus early drug release may occur. Another useful polymer is polyvinyl acetate phthalate (PVAP) which is less permeable to moisture and gastric fluid, more stable to hydrolysis and able to dissolve at a lower pH, which could also result in early release of nicotine in the duodenum.

Another available polymer is hydroxypropyl methylcellulose phthalate. This has similar stability to PVAP and dissociates in the same pH range. Further examples of currently used polymers are those based on methacrylic acid, e.g., methacrylic acid ester copolymers with acidic ionizable groups, such as Eudragit L (particularly L30D) and S (methacrylic acid copolymer) and mixtures thereof. Dosage forms coated with Eudragit™, which dissolve in the ileum at about pH 6.8, and in the terminal ileum and caecum at about pH 7.2, have been developed for delivery of 5-aminosalicylic acid, and are particularly preferred in accordance with the invention. These coatings will deliver most of the active for absorption in the colon, although some will be absorbed at the site of dissolution of the coating (e.g. terminal ileum and/or caecum).

In a preferred embodiment a capsule is enteric coated and contains a plurality of granules containing the active agent which also are enterically coated. The enteric capsule coating is insoluble in the pH medium of the stomach, but dissolves in the pH of the small intestine, preferably the ileum, to release the enterically coated granules. These coated granules are insoluble in intestinal juice below about pH 7, but are soluble in colonic intestinal juice. The beads have different enteric coated polymers and thicknesses of coatings to provide a sustained release of the active agent for absorption from the colon. Suitable coatings are Eudragit L, S, R, L, RL and RS. A capsule such as above is described in more detail in U.S. Pat. No. 5,401,512 and WO-A-9214452, the teachings of which are incorporated herein by reference.

In another preferred oral dosage form, the active agent is complexed with a carbomer which is itself coated with an acrylic resin and contained in an enterically coated capsules. The capsule coating dissolves in the intestinal juices such as those of the small intestine, preferably the ileum, to deliver the active agent/carbomer complex to the colon.

A suitable alternative formulation would be to incorporate the nicotine or its salts, more preferably the nicotine carbomer complex, into heat-meltable ampiphilic excipients such as partial glycerides and polyglycerides of fatty acids of the Gelucire™ type (available from Gattefosse, France) or polyoxyethylene glycols, filled into hard gelatine capsules and coated with either cellulose derivative or acrylic polymer enteric coating.

Carbomers are available as fine white powders which disperse in water to form acidic colloidal suspensions (a 1% dispersion has approx. pH 3) of low viscosity. Neutralisation of these suspensions using a base, for example sodium, potassium or ammonium hydroxides, low molecular weight amines and alkanolamines, results in the formation of clear translucent gels. Nicotine and its salts form stable water-soluble complexes with carbomers at about pH 3.5 and are stabilised at an optimal pH of about 5.6.

Preferably, the carbomer is Carbopol. Such polymers are commercially available from B. F. Goodrich under the designation Carbopol™ 420, 430, 475, 488, 493, 910, 934, 934P, 974 and 974P. Carbopols are versatile controlled-release polymers, as described by Brock (Pharmacotherapy, 14;430–7(1994)) and Durrani (Pharmaceutical Res. (Supp.) 8;S-135 (1991)), and belong to a family of carbomers which are synthetic, high molecular weight, non-linear polymers of acrylic acid, crosslinked with polyalkenyl polyether. In a particularly preferred embodiment the carbomer is Carbopol™ 974P NF.

To prepare, for example, a nicotine/carbomer complex the carbomer is suspended in a appropriate solvent, such as water, alcohol or glycerin. Preferably, the carbomer is mixed with water, preferably de-ionised water. Mixtures may range, for example from 0.002 to 0.2 g of carbomer per ml of solvent, preferably from 0.02 to 0.1 g of carbomer per ml of solvent. The mixture is stirred thoroughly at room temperature until a colloidal suspension forms. The dispersion may be stirred using a suitable mixer with a blade-type impeller, and the powder sieved into the vortex created by the stirrer using a 500 micron brass sieve. This technique allows ample wetting of the powder and prevents the powder from forming a cluster of particles which then become difficult to wet and disperse.

The nicotine or nicotine salt may be diluted with any pharmaceutically acceptable organic solvent. In a preferred embodiment, the solvent is an alkanol such as ethanol. Mixtures may range, for example, from 0.01 to 10 g of nicotine per ml of solvent, preferably from 0.5 to 5 g of nicotine per ml solvent. This solution is then added drop wise to the carbomer suspension and mixed continuously until a gel of uniform consistency has formed. Preferably, the nicotine/complex is made by combining 1 g of nicotine or nicotine salt with from 0.1 to 100 g of carbomer, more preferably with 1 to 50 g of carbomer. A gradual thickening of the suspension occurring as neutralisation of the carbomer takes place. The preparation will now take on the appearance of a slightly white translucent gel. This physical change in viscosity and appearance is consistent with neutralisation of the acid by the base.

The gel is then dried. According to one embodiment, the gel is vacuum dried. By way of example, the gel is spread on a glass plate and dried under vacuum at 50° C. for about 24 hours. Alternatively, the gel may be freeze-dried. Such methods are well known in the art.

Nicotine/carbomer complexes can then be formed into solid dosage forms and a pharmaceutically acceptable coating may be applied, as described above for non-complexed nicotine. For example, the complex may be enterically coated thereby delaying the release of the nicotine/carbomer complex until it reaches the ileum and colon.

Alternatively the gel can be incorporated into a suitable liquid enema formulation as described earlier.

The invention will be illustrated by way of the following non-limiting examples, and drawings.

EXAMPLE 1

Figure 2:
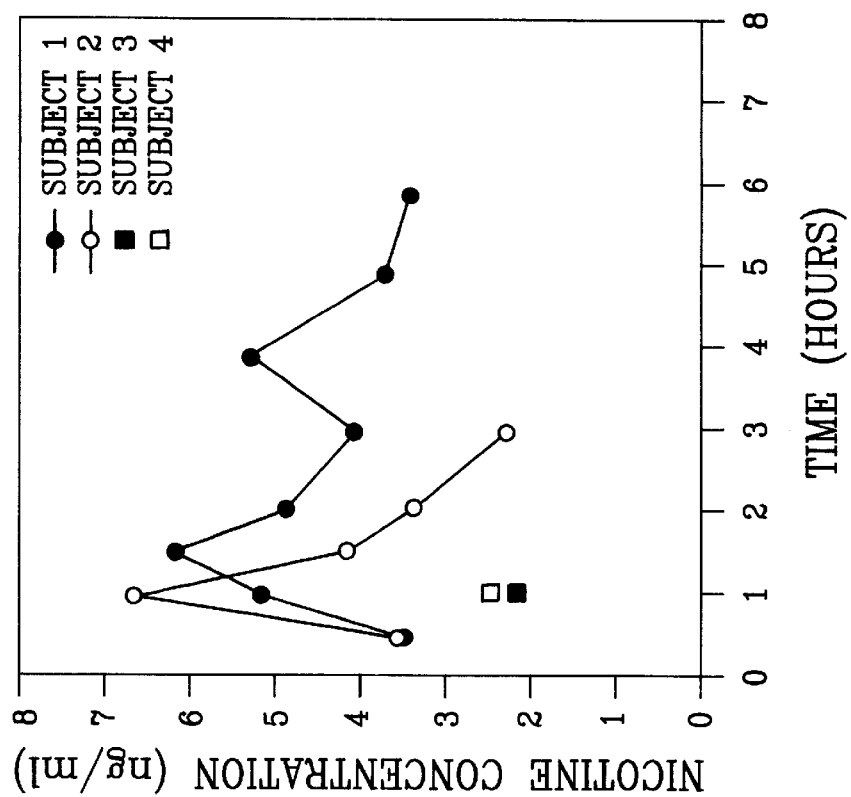
FIG. 2 shows plasma concentration-time curve after oral administration of 45 mcg nicotine/Kg body weight for each subject with detectable levels (2 subjects had no detectable levels).

The levo(-) form of nicotine base was used to prepare nicotine/carbomer capsules. Nicotine was obtained from Sigma Chemicals at a 98–100% purity and a density of 1.02 g/ml. It was protected from light and stored in a cool place.

Carbopol™ 974P NF (1 g 13.2 mmol carboxylic acid) was mixed with 50 ml of de-ionised water; stirred thoroughly and allowed to stand for 30 minutes at room temperature. Meanwhile, nicotine (1 g 17 drops from a Pasteur pipette) was diluted in 1 ml absolute ethanol. This solution was then added dropwise to the carbomer suspension and mixed continuously for approximately 10 minutes until a gel of uniform consistency had formed. Visual observation, during this process, noted a gradual thickening of the suspension occurring as neutralisation of the carbopol took place. It was also accompanied by a white appearance of the product. This physical change in viscosity was consistent with neutralisation of the acid by the base.

The gel was then spread on a large glass plate and dried under vacuum at 50° C. for 24 hours. The resulting white crystalline material was crushed using a pestle and mortar. The yield was 1.45 g (72.5%) after prolonged drying of the ground crystals.

An alternative method of drying to elevated temperature is freeze-drying. On repeating the above manufacture and freeze-drying the product, the yield increased to 1.65 g (82.5%). This yield increase was probably due to reduced volatilisation of the nicotine component.

Larger batches were prepared as follows: 50 g of carbopol powder was weighed and dispersed in 2500 ml of de-ionised water. The dispersion was rapidly stirred using a suitable mixer with a blade-type impeller.

The powder was slowly sieved into the vortex created by the stirrer using a 500 micrometer brass sieve. Meanwhile, 1 g of nicotine was accurately measured and diluted with 1 ml of absolute ethanol. After the carbomer powder had been allowed to form a colloidal suspension for 30 min., the stirring speed was greatly reduced to get rid of the majority of air bubbles that had formed throughout the preparation. The alcoholic nicotine solution was then added drop wise into the vortex and stirring continued for 60 min. At the end of this time the batch was freeze-dried. This product could then be used to prepare coated capsules or enemas in accordance with the invention.

EXAMPLE 2

A carbomer colloidal suspension was prepared as described above by dissolving 200 mg to 800 mg, preferably 400 mg of Carbopol™ 974P in de-ionised water. To this suspension was added dropwise a nicotine/ethanol solution (2 to 12 mg nicotine base). A xanthan gum solution of 75 mg to 400 mg, preferably (100 mg of xanthan gum e.g. Keltrol™; 150 mg methyl hydroxybenzoate; and 15 mg propyl hydroxybenzoate) was then added to the complex. Trometamol can optionally be added as a thickening and buffering agent. In this example the pH was then adjusted to 5.5 and the viscosity to 4.35 mNa by adding the required quantity of a 1% w/v aqueous trometamol solution. The final volume was adjusted to 100 ml.

When trometamol is used as a buffer instead of e.g. phosphate buffer, the nicotine peak plasma concentration is significantly lowered. Since nausea and other side-effects are induced by peak plasma levels, this decrease further improves the beneficial treatment of the invention.

EXAMPLE 3

Part A

Delayed-release Eudragit™ coated oral nicotine capsules were prepared by Tillotts Pharma AG, Ziefen, Switzerland and consisted of either 3 mg or 6 mg of nicotine (8.887 mg or 17.774 mg nicotine tartrate base salt, respectively). The nicotine salt was suspended in an excipient (a saturated polyglycolized glyceride; Gelucire™ 44/14, (supplied by Gattefosse France) (190 mg or 380 mg respectively) and filled into hard gelatine capsules (size 1). The capsules were then coated with Eudragit™ L30D. Eudragit™ L30D is a polymer which dissolves at about pH 6.8 in the ileum. The size of the capsule and the thickness of the Eudragit coating are similar to those used to deliver Asacol™ (Eudragit coated mesalamine) to the terminal ileum (Schroeder et al., NEJM, 317:1625–9 (1987)).

Part B

Delayed-release Eudragit coated oral nicotine/carbomer capsules were prepared by Tillotts Pharma. Nicotine/carbomer powder (1:50—nicotine carbomer) was coated with Eudragit™ L, S or LS. The coated powder was then formed into spherules, coated with Eudragit S and filled into hard gelatine capsules (size 1). The capsules were then coated with Eudragit™ L30D. In one example, the capsules contained 150 mg nicotine-carbomer complex, equivalent to 3 mg nicotine base.

EXAMPLE 4

This study compared the bioavailability and pharmacokinetics parameters of nicotine after administration by each of 6 different routes: IV; oral; hydrophilic enema (acidic and basic); and hydrophobic enema (acidic and basic).

Intravenous nicotine was prepared using a nicotine base, supplied as the tartrate salt (Fisher Scientific/Eastman Kodak Company, Rochester, N.Y.). Solutions for injection were made up by combining 1.5 mg nicotine base (4.44 mg tartrate salt) in 100 ml of 0.9% sterile normal saline to form a 15 mcg/mL solution. The intravenous solution was filtered through a 0.22 micron filter into a sterile container and under sterile conditions. The solution was then cultured for organisms, assayed for endotoxin, and chemically analyzed prior to infusion to assure stable nicotine concentration. These samples were then be stored in sealed vials until the time of administration.

The oral preparation was formed by dissolving 45 micrograms nicotine base/kg body weight (133.3 micrograms tartrate salt/kg body weight) in 30 ml purified water. This dosage (approximately 3 mg nicotine base for a 70 kg subject) has been well-tolerated in a previous study in which oral nicotine was administered (Benowitz et al., *Clin. Pharmacol. Ther.* 49:270–7 (1991)).

The hydrophilic enema vehicle was prepared by combining 500 mg of medium viscosity carboxymethylcellulose (Spectrum Chemical Manufacturing Corporation, Gardina, Calif.), 5 g sorbitol (Spectrum Chemical), and 60 mL of water. The sorbitol was added to make the vehicle isoosmolar and the carboxymethylcellulose was used as a suspending agent. The vehicle, described previously (Sandborn et al., *J. Clin. Pharmacol.* 31:76–80 (1991)), was dispensed into 120 ml enema bottles. The active agent, 133.3 micrograms nicotine tartrate salt/kg body weight (equivalent to 45 micrograms nicotine base/kg body weight) was added to the enema vehicle.

The hydrophobic enema vehicle was prepared by adding 3 g of Witepsol H-15 (an oleaginous base—Huls American Inc., New Jersey) to the hydrophilic enema vehicle. Enema vehicles were made acidic by adding 5.06 g of sodium citrate dihydrate (Spectrum Chemical) and 0.56 g of citric acid monohydrate (Spectrum Chemical) to create a solution with a pH of 5.5. Enema vehicles were made basic by adding 5.23 g of sodium phosphate (Spectrum Chemical) and 0.05 g of sodium phosphate monobasic (Spectrum Chemical) to create a pH 8.5 solution. The enema vehicles were confirmed to be stable over a 48 hour time period (100% recovery) with a minimal decrease in nicotine concentration when allowed to stand at room temperature over a 3 week period (97% recovery at 1 week, 94% recovery at 2 weeks, 91% recovery at 3 weeks).

Thirty paid human volunteers were admitted to the pharmacokinetic study after giving informed consent to a protocol approved by the institutional review board at the Mayo Clinic, Rochester, Minn. The subjects ranged in age from 21–56 and their body weights ranged from 45 to 153 Kg. All subjects were non-smokers and were healthy based on their histories, and physical examination. Subjects agreed to practice birth control during the study period. Complete blood count, chemistry group, urinalysis and pregnancy test (women only) were obtained. Subjects were excluded if they had cardiovascular disease, peripheral vascular disease, hypertension, were nursing mothers, had laboratory evidence of pregnancy, or had hepatic or renal dysfunction.

Based on the results of a pilot study of two additional subjects, it was determined that colonic absorption of nicotine is dependent upon patient position, with higher plasma levels detected when subjects were allowed into a sitting position immediately after administration, rather than remaining in the left lateral decubitus position. The first subject studied underwent 3 investigations (IV, 15 mcg/Kg hydrophilic basic enema, 45 mcg/Kg hydrophilic basic enema). During the 15 mcg/Kg enema visit the subject was inadvertently allowed into a sitting position after administration and was found to have an AUC of 17 (ng)(hr)/mL (IV visit AUC 18 (ng)(hr)/mL) with a bioavailability of 94%. On the 45 mcg/Kg visit the subject remained in the left lateral decubitus position the entire time the enema was retained and had an AUC of 0 (ng)(hr)/mL with a bioavailability of 0%. Similarly, one subject withdrew from the study after the enema visit (first visit) in which an upright position was taken shortly after administration and side effects occurred. The AUC for this subjects visit was 18 (ng)(hr)/mL. During the remainder of the study, subject position was more closely monitored and plasma nicotine concentrations remained low or undetectable with enema administration.

Each subject underwent 2 investigations (IV and non-IV) of 8 hours duration at least 1 week apart. During the IV visit, subjects were given a 15–30 minute infusion of the IV nicotine solution (15 mcg/Kg dose). During the non-IV visit subjects were given a 45 mcg/Kg dose of nicotine base via one of five randomly selected delivery routes which were prepared within 48 hours of administration: oral; hydrophilic enema (acidic or basic); hydrophobic enema (acidic or basic). The subjects were instructed to remain in the left lateral decubitus position while the enema was retained and to retain the enema for at least one hour. On each study day, venous blood samples were drawn from an IV catheter into standard chemistry vacutainer tubes. Samples were obtained before nicotine administration and at the following time points (time=0 was defined as the point at which the nicotine infusion was started or the non-IV dose was administered): 5, 10, 15, 30, 60, 90 minutes, and 2, 3, 4, 5, 6, and 8 hours. Whole blood samples were centrifuged and plasma samples were then stored at −20 degrees Celsius until analysis. Plasma concentrations of nicotine were determined by gas chromatography/mass spectrometry as described by Baskin et al. (*Clin. Chem.,* 31:76–80 (1991)).

For this study, the maximum plasma nicotine concentration ($C_{max}$) and the time to reach $C_{max}$ ($T_{max}$) were defined as the highest measured plasma concentrations and the time of the sample, respectively. The following pharmacokinetics parameters were calculated using standard equations (Gibaldi (ed.) Pharmcokinetics 2nd ed, Marcel Dekker Inc., New York 409–17 (1982)): area under the plasma nicotine concentration versus time curve (AUC), bioavailability (F), blood elimination half-life (T½), volume of distribution (Vdss), and blood nicotine clearance (Clb).

The computed bioavailability for each subject was used in an analysis of covariance to compare the five groups. Within subject (IV versus non-IV) variation was evaluated for each group of 6 subjects using a paired-T test. In addition, data was reviewed for gender variation.

Figure 1:
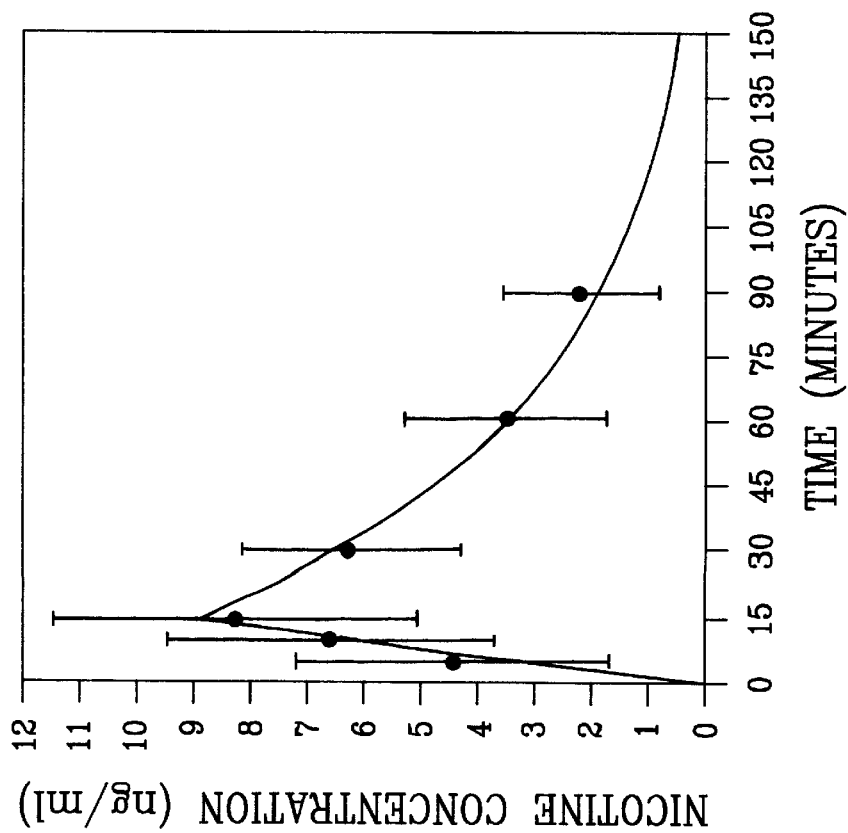
FIG. 1 shows mean plasma concentration-time curve during intravenous administration of 15 mcg nicotine/Kg body weight over 15–30 minutes.
Figure 4:
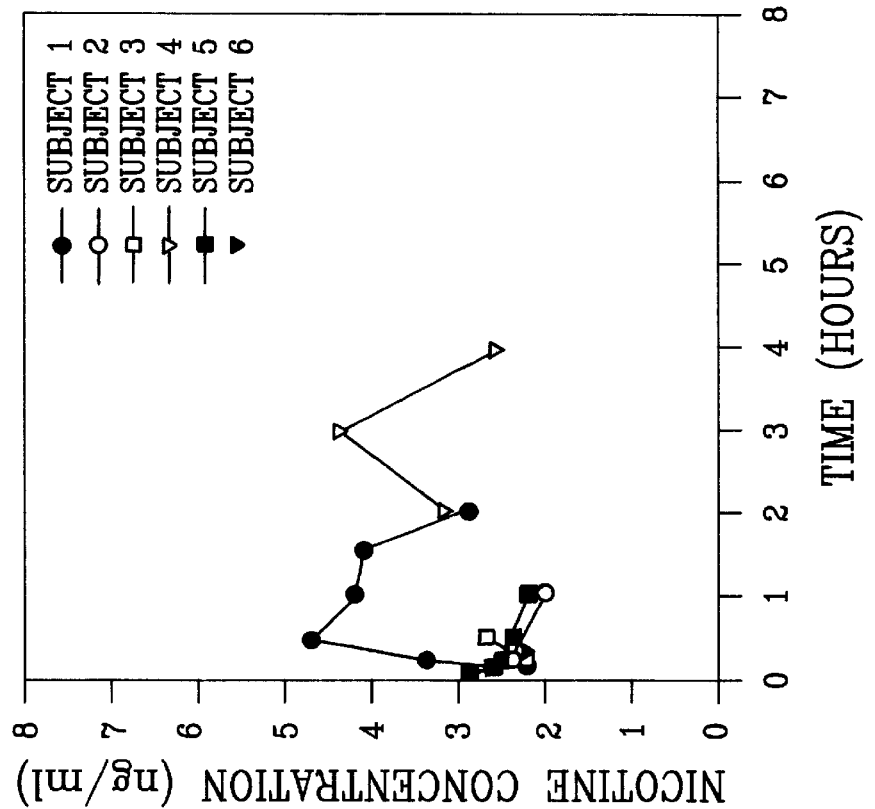
FIG. 4 shows plasma concentration-time curve after administration via hydrophilic basic enema vehicle of 45 mcg nicotine/Kg body weight for each subject with detectable levels (1 subject had no detectable levels).
Figure 3:
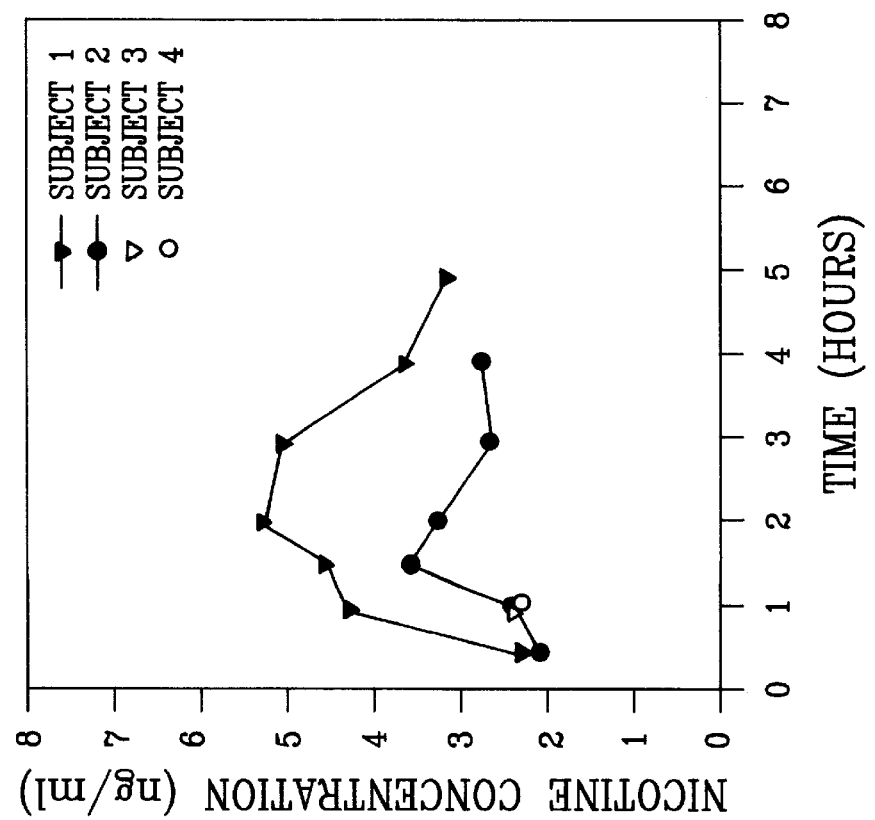
FIG. 3 shows plasma concentration-time curve after administration via hydrophilic acidic enema vehicle of 45 mcg nicotine/Kg body weight for each subject with detectable levels (2 subjects had no detectable levels).
Figure 6:
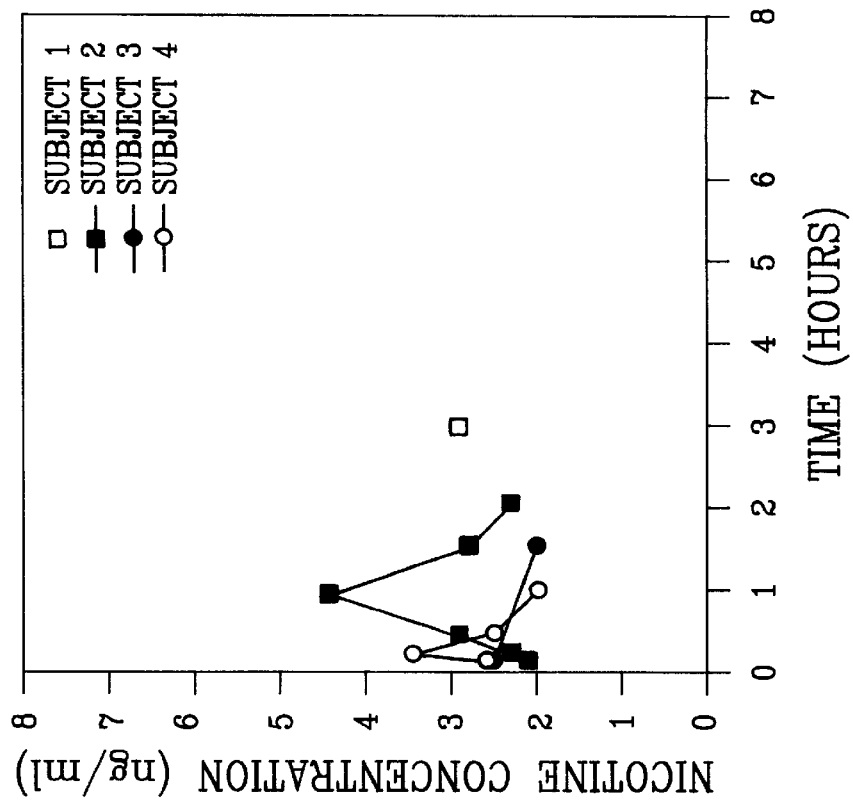
FIG. 6 shows plasma concentration-time curve after administration via hydrophobic basic enema vehicle of 45 mcg nicotine/Kg body weight for each subject with detectable levels (2 subjects had no detectable levels).
Figure 5:
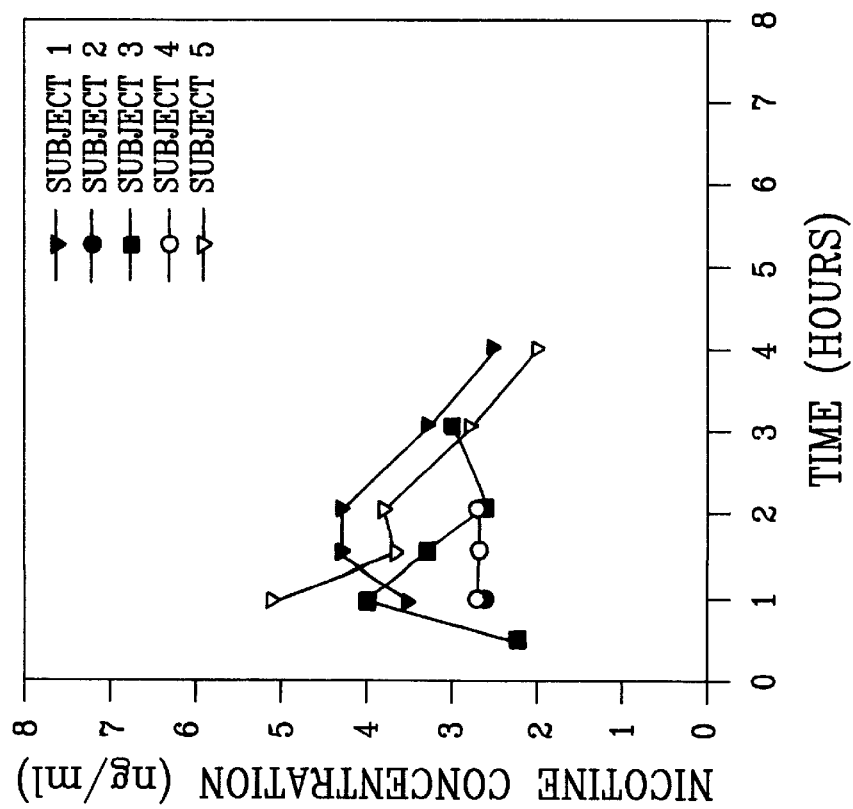
FIG. 5 shows plasma concentration-time curve after administration via hydrophobic acidic enema vehicle of 45 mcg nicotine/Kg body weight for each subject with detectable levels (1 subject had no detectable levels).

Mean plasma nicotine concentrations after IV is shown in FIG. 1. Plasma nicotine concentrations after oral, hydrophilic acidic enema, hydrophilic basic enema, hydrophobic acidic enema, and hydrophobic basic enema are shown in FIGS. 2 through 6, respectively. Nicotine was first detected in the plasma at 30 minutes with oral, hydrophilic acidic enema, and hydrophobic acidic enema administration, 10 minutes with hydrophobic basic enema administration, and 5 minutes with hydrophilic basic enema administration (when detectable levels were present).

The mean values for the pharmacokinetics parameters and statistical probability by analysis of covariance for nicotine administered by each of the various routes are shown in Table 1. No statistical differences were found in $C_{max}$, AUC, and bioavailability when comparisons were made between enema and oral administration; however, $T_{max}$ for the hydrophilic basic enemas was significantly earlier than for the other 4 delivery systems. Finally, the mean bioavailability for the various routes of administration are as follows: oral 19%; hydrophilic acidic enema 16%; hydrophilic basic enema 14%; hydrophobic acidic enema 25%; hydrophobic basic enema 15%.

TABLE 1

| | Subjects (n) | AUC[+] (ng)(h)/mL | F % | $T_{max}$ hr | $C_{max}$ ng/mL |
|---|---|---|---|---|---|
| Oral | 6 | 9 ± 5 | 19 ± 10 | 1.1 ± 0.1 | 3 ± 1 |
| Hdrphbc Acid | 6 | 10 ± 3 | 25 ± 7 | 1.3 ± 0.2 | 3 ± 1 |
| Hdrphbc Base | 6 | 4 ± 1 | 15 ± 4 | 1.1 ± 0.5 | 2 ± 1 |
| Hrdrphlc Acid | 6 | 8 ± 4 | 16 ± 7 | 1.4 ± 0.2 | 2 ± 1 |
| Hrdrphlc Base | 6 | 4 ± 2 | 14 ± 6 | 0.3 ± 0.1 | 2 ± 1 |
| P* | | 0.834 | 0.830 | 0.023 | 0.885 |

*Analysis of covariance adjusting for baseline.
[+]Analyzed on the natural log scale.
IV nicotine studies (n = 32) (mean ± SD):
AUC = 12 ± 5 (ng)(hr)/mL;
$C_{max}$ = 9 ± 3 ng/mL;
$T_{max}$ = 0.3 ± 0.1 h.

Intraindividual side effects occurred during each study, as determined by a questionnaire filled out every 30 minutes, closely correlated with plasma nicotine concentrations. However, the threshold above which symptoms appeared varied from individual to individual with the nicotine concentration at which side effects first appeared ranging from 2.4 ng/mL to 9.9 ng/mL (although some subjects had nicotine concentrations of >11 ng/mL without symptoms). When side effects occurred, they consisted of nausea lightheadedness, and diaphoresis with variable frequency.

During the course of the study, it was observed that the systemic bioavailability of the enema vehicles appeared to be highly dependent upon the position in which the subject remained while retaining the enema. Subjects that were allowed to sit upright shortly after enema delivery were observed to have a higher bioavailability than when remaining in the left lateral decubitus position. This presumably was due to rectal pooling of the enema with absorption directly into the systemic circulation rather than the portal circulation, thereby eliminating first pass metabolism by the liver. By virtue of the positional dependence of this preparation, formulation of a colonic delivery system which could avoid direct absorption by the hemorrhoidal circulation could be beneficial.

In summary, rectally administrated and DRO compositions of nicotine had low bioavailability and was well tolerated. Therefore, nicotine may be administered to the colon as a therapeutic agent for the treatment of nicotine responsive conditions, particularly those given hereinbefore, while reducing the limitations inherent to other modes of administration.

EXAMPLE 5

The aim of this study was to determine nicotine tartrate pharmacokinetics after administration by: IV, and 3 mg and 6 mg Eudragit S coated delay release oral (DRO) capsules.

Twenty subjects were randomly assigned to 1 to 2 groups (each n=10); 3 mg and 6 mg nicotine tartrate DRO. Each subject had 2 studies [DRO and 15 μg/kg (mean 1 mg) IV] separated by >1 week with the order (IV vs DRO first) randomly assigned. After nicotine administration, blood was obtained for 12 hours and serum nicotine was determined by gas chromatography/mass spectrometry. Plasma cotinine concentrations were determined HPLC in 2 subjects (both 6 mg) over 72 hours. Pharmacokinetic parameters determined were: maximum concentration (Cmax); time to Cmax (Tmax); area under the curve (AUC); bioavailability (F); volume of distribution (Vdss); clearance (CL); and half-life (T½).

Delayed-release Eudragit coated oral nicotine capsules were prepared in accordance with Example 3, Part A.

Delayed-release Eudragit coated oral nicotine/Carbopol capsules were prepared in accordance with Example 3, Part B.

The results of the study are shown in Table 2.

TABLE 2

| Group | No. | AUC ng*h/mL | F % | Cmax ng/mL | Tmax h | Vdss L/kg | CL L/kg/h | T½ h |
|---|---|---|---|---|---|---|---|---|
| 3 mg | 10 | 21 ± 15 | 41 ± 30 | 7 ± 6 | 4.8 ± 1.5 | | | |
| 6 mg | 10 | 42 ± 20 | 42 ± 20 | 10 ± 4 | 5.3 ± 1.1 | | | |
| IV 1 mg | 20 | 20 ± 11 | 100 ± 0 | 10 ± 2 | 0.4 ± 0.1 | 2 ± 1 | 1 ± 1 | 1 ± 1 |
| P | | 0.02 | 0.93 | 0.18 | 0.38 | | | |

The ratios of cotinine AUC after 6 mg DRO and IV nicotine were 1.5 (2036/1401) and 1.6 (3176/2002) for the 2 subjects undergoing cotinine pharmacokinetics, demonstrating significant first pass metabolism.

The results show that nicotine tartrate administered to the ileocolon by the DRO route reduced systemic bioavailability of nicotine, apparently as a result of first pass metabolism to cotinine. Since systemic cotinine is a less active metabolite than nicotine, this could partly explain the reduced side-effects achieved with the invention.

Therefore a sustained DRO composition of nicotine can be used for the treatment of nicotine responsive conditions while reducing the side-effects and disadvantages inherent in other known modes of nicotine delivery.

EXAMPLE 6

Eight normal healthy volunteers and 8 patients with active UC were enrolled in this open label, single dose study.

Enemas were formulated which contained 2, 6 and 12 mg of nicotine, 400 mg of Carbopol, 100 mg of xanthan gum (Keltrol) to increase viscosity, 150 mg methyl hydroxybenzoate and 15 mg propyl hydroxybenzoate and deionised water to make up to 100 ml; phosphate buffer (pH 7.5) was added to produce a final pH of 5.5 with the effect of to increasing nicotine's stability. The nicotine content of sample enemas was first confirmed by diluting a small volume of the contents in dilute hydrochloric acid to produce an approximate concentration of 30 ng/ml, which could then be accurately measured by our assay.

Side-effect experienced by the subjects were recorded as absent, mild, moderate or severe. Subjects were asked to report the time, nature and severity of any symptoms, at the commencement and each hour through the study, and were questioned particularly about nausea, vomiting, lightheadedness, tremor, palpitations and headache. Blood pressure and pulse rate were also recorded each hour and when any symptoms occurred.

Five of the subjects, 4 normal and one patient reported side-effects. These occurred in five out of eight females and 5 of the 8 lifelong non-smokers. Those with higher $C_{max}$ values for nicotine and lower body weights were more likely to report side effects. The average onset of symptoms was about 20 minutes after administration of the enema, range 15–30 and lasted for a mean of 58 minutes, range 45–70 minutes. All 5 subjects felt lightheaded, 2 also experienced nausea and one had a headache. All symptoms were mild with the exception of one with moderate nausea; they were self limiting and not associated with changes in the pulse rate or blood pressure.

Administration of nicotine to the colon gives particularly few side-effects because only modest rises in serum nicotine occur. Strikingly side effects were few and the preparation well tolerated. The complex of nicotine with a polyacrylic carbomer delays release of the nicotine thereby further contributes to reducing any side effects.

In conclusion, whereas the use of nicotine gum and nicotine patch gave rise (in many patients) to intolerable side-effects, the inventors surprisingly found that absorption form the intestine more preferably delivery to the terminal ileum for colonic absorption (oral delivery), colon (oral and rectal delivery) or rectum (rectal delivery) of this highly toxic drug considerably reduced the side-effects (Table 7).

Without being bound by theory, the inventors believe that the side-effects are related to the maximum peak concentration and the rate of rise of nicotine in the systemic circulation. The low bioavailability of nicotine absorbed through the intestinal mucosa appears to be largely due to its conversion to the major metabolite cotinine on first pass metabolism in the liver. This occurs as the nicotine is taken up in the portal vein from the intestine to the liver before entering the systemic circulation. Thus the high peak plasma levels which are normally responsible for the adverse effects associated with nicotine are limited and therefore nicotine can be used therapeutically in a safer and more convenient manner.

When the nicotine is delivered in the form of a complex with polyacrylate, and/or with Gelucire™, particularly as a DRO composition, the plasma levels are further limited thereby further decreasing any remaining side-effects and increasing patient comfort. Furthermore when trometamol is used as a buffer in a nicotine-carbomer enema there appears to be some unexplained synergy in that the peak plasma levels and thus side-effects are minimised so that even slightly built patients are not troubled by side-effects.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention as defined in the following claims.

What is claimed is:

1. In a method for treating a nicotine-responsive condition which is not inflammatory bowel disease comprising administering to a patient an effective amount of an active compound selected from the group consisting of pharmacologically acceptable derivatives of nicotine, the improvement which comprises administering to the patient as a post-gastric delayed release oral composition a unit dosage form which is a pill, tablet, powder or capsule containing an effective amount of about 1 to about 36 mg per unit dosage form of a pharmacologically acceptable nicotine salt or nicotine polyacrylate complex which is enteric coated with polymer so as to be released at intestinal pH.

2. The method of claim 1 where the nicotine responsive condition is selected from the group consisting of inflammatory skin conditions, schizophrenia, Alzheimer's disease, Parkinson's disease, Tourette's syndrome, and addiction to smoking.

3. In a method for treating a nicotine-responsive condition which is not inflammatory bowel disease comprising administering to a patient an effective amount of an active compound selected from the group consisting of pharmacologically acceptable derivatives of nicotine, the improvement which comprises rectally administering to the patient an effective amount of about 0.001 to about 1.5 mg/kg (calculated as nicotine free base) of an active compound which is a nicotine/carbomer complex in a flowable liquid carrier as an enema.

4. The method of claim 3 where the nicotine responsive condition is selected from the group consisting of inflammatory skin conditions, schizophrenia, Alzheimer's disease, Parkinson's disease, Tourette's syndrome, and addiction to smoking.

5. The method of claim 2 wherein the composition comprises said nicotine salt or nicotine-polyacrylate complex in an excipient of a saturated polyglycolized glyceride.

6. The method of claim 2 wherein the enteric polymer coating dissolves in the terminal ileum.

7. The method of claim 2 wherein the active compound is predominantly absorbed from the colon.

8. The method of claim 2 wherein the active compound is nicotine-polyacylate complex which is nicotine complexed with a polyacrylic acid polymer.

9. The method of claim 8 wherein the polyacrylic acid polymer is a carbomer.

10. The method of claim 5 wherein the polyglycolized glyceride excipient is Gelucire™.

11. The method of claim 6 wherein the enteric polymer coating is Eudragit™.

12. The method of claim 11 wherein the unit dosage form is a capsule containing a nicotine-polyacylate complex in a polyglycolized glyceride excipient and coated with Eudragit™ L as the enteric coating.

* * * * *